United States Patent [19]

Bistline, Jr. et al.

[11] 4,116,986

[45] Sep. 26, 1978

[54] PROCESS FOR SULFATING FATTY ALKANOLAMIDES

[75] Inventors: Raymond G. Bistline, Jr., Wyndmoor; Warner M. Linfield, Oreland; Wilfred R. Noble, Wyndmoor, all of Pa.

[73] Assignee: The United States of America as represented by the Secretary of Agriculture, Washington, D.C.

[21] Appl. No.: 794,596

[22] Filed: May 6, 1977

[51] Int. Cl.$^2$ ........................ C07C 143/90; C11D 1/28

[52] U.S. Cl. .................................................. 260/401

[58] Field of Search ......................................... 260/401

[56] References Cited

U.S. PATENT DOCUMENTS

| | | | |
|---|---|---|---|
| 1,932,178 | 10/1933 | Guenther | 260/401 |
| 1,981,792 | 11/1934 | Orelup | 260/401 |
| 2,353,081 | 7/1944 | Robinson | 260/401 X |
| 2,478,368 | 8/1949 | Caldwell | 260/401 |

*Primary Examiner*—Winston A. Douglas
*Assistant Examiner*—John F. Niebling
*Attorney, Agent, or Firm*—M. Howard Silverstein; William E. Scott; David G. McConnell

[57] ABSTRACT

The process for sulfating fatty alkanolamides prepared from the reaction of fatty acids and esters with low molecular weight alkanolamines is improved by adding about 5 to 15% by weight of a low molecular weight alcohol to the fatty alkanolamide and consulfating with a sulfating agent.

8 Claims, No Drawings

PROCESS FOR SULFATING FATTY ALKANOLAMIDES

BACKGROUND OF THE INVENTION

1. Field of the Invention

This invention relates to sulfated fatty alkanolamide surfactants and more particularly to a process for producing fatty alkanolamides which are completely or almost completely sulfated.

2. Description of the Prior Art

Sulfated fatty alkanolamides were first synthesized some years ago and found to be effective detergents (U.S. Pat. Nos. 1,932,180 and 1,981,792). However, according to the prior art (Manufacturing Chemist 28, 124, 1957), it is extremely difficult to control sulfation to insure that the product is free of undesirable by-products which impair its efficiency as a detergent. It is well known that fatty alkanolamides are not usually sulfated maximally. Following are some of the difficulties that explain why they are so poorly sulfated: (1) the high viscosity of the molten alkanolamides prevents effective mixing with the sulfating agent; (2) the resulting unneutralized sulfated alkanolamides are even higher melting and much more viscous than the alkanolamides so that intimate contact with the sulfating agent is increasingly impeded; and (3) neutralization of such, hot viscous material is difficult and slow, and a substantial amount of hydrolysis may occur during this step. Although the viscosity problems can be partially alleviated by sulfation at high temperatures, this leads to charring and side reactions (U.S. Pat. No. 2,551,125). The viscosity problem can also be alleviated or even eliminated by the use of large amounts of inert solvents such as dichloroethane, methylene chloride, carbon tetrachloride or 1,1,1-trichloroethane. However, removal of solvents from such surfactant solutions is difficult and impractical on a commercial scale.

Consequently, even though the sulfated fatty alkanolamides are well known for their superior detergency and lime soap dispersing ability, they have not been produced in large volume because of the extreme difficulty in controlling the sulfation process to insure maximum sulfation and freedom of the sulfated product from undesirable by-products. With presently available processes, the maximum yield of sulfation is usually from 75-85% and the sulfated product contains large amounts of undesirable inorganic salts and organic by-products. As a result, these products exhibit inferior detergency and are not desirable for use in household detergents.

SUMMARY OF THE INVENTION

An object of this invention is to provide a process for producing fatty alkanolamides which are completely sulfated.

Another object of this invention is to provide a process for preparing sulfated alkanolamides which does not require the use of chlorinated solvents.

Still another object is to provide a process for preparing sulfated alkanolamides which does not require the use of high temperatures.

In general, the above objects are accomplished by an improvement in the process of sulfating a fatty alkanolamide wherein from about 5 to about 15% by weight of a low molecular weight alcohol is added to the alkanolamide and the alcohol and alkanolamide are cosulfated with a sulfating agent. The low molecular weight alcohol is chosen from those having from 1 to 8 carbon atoms.

DETAILED DESCRIPTION OF THE INVENTION

The process of this invention is characterized by the cosulfation of small amounts of low molecular weight alcohols with fatty alkanolamides. The addition and cosulfation of these alcohols with the alkanolamides increases the fluidity of the sulfated fatty alkanolamide in the acid form and makes it easier to rapidly neutralize the alkanolamide. The improvement of this invention does not require special apparatus; the process is readily carried out in conventional sulfation equipment.

Fatty alkanolamides may be prepared from individual $C_{10}$–$C_{18}$ fatty acids or their methyl esters as, for example, decanoic, lauric, myristic, palmitic, stearic, and oleic, or mixtures of fatty acids such as those derived from animal fats or vegetable oils, that is, tallow, coconut oil, palm oil, palm kernel oil, fish oils, etc. These can readily be reacted with a variety of low molecular weight alkanolamines as, for exampe, monoethanolamine, mono-n-propanolamine, monoisopropanolamine, diglycolamine (2-(2-aminoethoxy) ethanol), 3-hydroxy-1-amino-butane, 4-hydroxy-1-amino butane, or amino-cyclohexanol, to produce the desired fatty alkanolamides. The fatty alkanolamide is prepared by heating the alkanolamine with either a fatty acid or a methyl ester of a fatty acid at 140°–150° C. for about 5 to 24 hours with the application of a slight vacuum. It is important that the finished amide be free from water and unreacted alkanolamine.

The fatty alkanolamides are waxes with high melting points. The ethanolamides of the $C_{12}$–$C_{18}$ fatty acids melt in the range of 85°–105° C.; the $C_{12}$–$C_{18}$ fatty n-propanolamides at 75°–97° C. and the $C_{12}$–$C_{18}$ fatty isopropanolamides at 70°–86° C. Sulfation on a large scale in a batch unit is awkward because the high viscosity of the molten amides impedes contact with the sulfating agent, and the sulfated products are even higher melting and more viscous than the amides themselves. Consequently, higher temperatures are required which leads to charring and other side reactions, and neutralization of such material is very difficult and extremely time consuming.

We discovered that the fatty alkanolamides may be readily and completely sulfated in the presence of small amounts of low molecular weight alcohols at a temperature range of from about 20° to about 50° C. The alkyl sulfates that are formed lower substantially the melting point of the sulfated fatty alkanolamide in the acid form, facilitate the neutralization of the alkanolamide and aid in producing a fluid product. The addition of 5 to 15% by weight of low molecular weight alcohols to the fatty alkanolamide reduces viscosity, thus allowing better contact with the sulfating agent. A sulfated tallow alkanolamide made by the process of this invention is fluid at 45° C. and is neutralized readily. The addition of small amounts of chlorinated solvents further facilitates the ease and the completeness of the sulfation of fatty alkanolamides by reducing the viscosity of the reaction mixture and permitting even more intimate contact of the reactants. In addition, the presence of small amounts of alkyl sulfates does not interfere with detergency or other surface active properties. The neutralized sulfated fatty alkanolamides, because of their lime soap dispersing ability, may readily be combined with soap into effective soap-based detergent formulations.

The improvement in the process of sulfating fatty alkanolamides that we claim as our invention is exemplified as follows using tallow isopropanolamide.

CO-SULFATION IN THE ABSENCE OF CHLORINATED SOLVENT

Example 1

A mixture of tallow isopropanolamide, 102.2g (0.31 mole) and methanol, 10g (0.31 mole) was heated with stirring to 45°-50° C. Chlorosulfonic acid, 79.7g (0.68 mole) was added slowly over a forty-five minute period. Upon completion of the acid addition a slight vacuum was applied for 30 minutes to remove hydrogen chloride gas. Potassium hydroxide, 47g (0.84 mole) was dissolved in a mixture of 30ml distilled water and 25g isopropanol. The sulfated reaction mass was then added slowly to the well agitated alkaline solution. The temperature was maintained at 40°-45° C. pH was adjusted to 9-9.5. The product was bleached with hydrogen peroxide (5g of a 30% solution). Yield: 263.3g of a solution containing 44.7% active ingredient corresponding to an 85% yield of sulfation.

The active anionic surfactant content was determined, in each of the examples, according to the method of Cahn, by titration with standard cationic surfactant with dichlorofluorescein as indicator (U.S. Pat. No. 2,471,861). Initially, chlorosulfonic acid reacts with hydroxyl group to form the sulfated alkanolamide. Excess chlorosulfonic acid will attack the unsaturated bonds of tallow forming a sulfonatosulfate which is also measured by the Cahn test. This may give rise to results of greater than 100% sulfation.

Example 2

A mixture of tallow isopropanolamide, 101.3g (0.31 mole) and isopropanol, 10g (0.17 mole) was caused to react with chlorosulfonic acid 61.5g (0.53 mole) under conditions described in Example 1 and neutralized with potassium hydroxide, 38g (0.68 mole) dissolved in 25ml distilled water and 25g isopropanol. Yield: 236.5g of a solution containing 50.6% active ingredient, representing an 86.6% yield.

Example 3

A mixture of tallow isopropanolamide, 100.1g (0.305 mole) and 2-butanol, 10g (0.135 mole) was sulfated with chlorosulfonic acid, 58.6g (0.50 mole) under conditions described in Example 1 and neutralized with potassium hydroxide, 40g (0.72 mole) dissolved in 30ml distilled water and 25g isopropanol. Yield 268.7g of a solution containing 39.2% active ingredient corresponding to a 77.3% yield of sulfation.

CO-SULFATION IN THE PRESENCE OF A CHLORINATED SOLVENT

Example 4

Tallow isopropanolamide, 504g, (1.53 mole) was melted and 1,1,1-trichloroethane, 120g, was added followed by isopropanol, 50g (0.84 mole). The mixture was maintained 40°-45° C. while chlorosulfonic acid, 331g (2.84 mole) was added slowly. After the addition was completed, agitation was continued for thirty minutes at 40°-45° C. while slight vacuum was applied to remove hydrogen chloride gas. In a separate vessel potassium hydroxide 195g (3.5 mole) was dissolved in 200ml distilled water and 200g isopropanol added. The sulfated reaction mass was then added slowly to the well agitated alkaline solution, the temperature of which was maintained at 40°-45° C. Additional alkali was added to bring the pH of the batch to 9-9.5. Hydrogen peroxide (5g of a 30% solution) was added to bleach the product to a light color. A yield of 1336g of a solution containing 48.2% active ingredient was obtained which corresponds to a 94.3% yield of sulfation.

Example 5

Tallow isopropanolamide, 50.8g (0.155 mole) was melted and 1,1,1-trichloroethane 20g, was added followed by methanol, 5.1g (0.156 mole). Sulfation with chlorosulfonic acid, 41g (0.375 mole) was carried out as described in Example 4 and neutralized with potassium hydroxide 27g (0.46 mole) dissolved in 20ml distilled water and 20g isopropanol. Yield: 160.4g of a solution containing 44.5% active ingredient which corresponds to a 100% yield of sulfation.

Example 6

Tallow isopropanolamide, 51.4g (0.156 mole) was melted and 1,1,1-trichloroethane, 20g and ethanol, 5.1g (0.109 mole) added. Sulfation with chlorosulfonic acid 38.2g (0.32 mole) was carried out as described in Example 4. Potassium hydroxide 27g (0.48 mole) dissolved in 20ml distilled water and 15g ethanol neutralized the sulfated amide to pH 9-9.5. Yield: 150.6g of a solution containing 50.5% active ingredient which corresponds to a 108% yield of sulfation. The yield figure indicates that some double bond sulfation has also occurred.

Example 7

Tallow isopropanolamide 53.2g (0.162 mole) was melted and 1,1,1-trichloroethane, 20g, and isobutanol, 5g (0.067 mole) were added. The sulfation was carried out as described in Example 4, using chlorosulfonic acid, 32.8g (0.28 mole). Yield: 133.3g of a solution containing 53.7% active ingredient which corresponds to a 100.2% yield of sulfation.

Example 8

Tallow isopropanolamide, 51.3g (0.156 mole) was melted and 1,1,1-trichloroethane, 40g and 2-ethylhexanol, 5.1g (0.039 mole) added with rapid stirring. Chlorosulfonic acid, 28.3g (0.24 mole) was used to carry out the sulfation as described in Example 4. Potassium hydroxide, 18g (0.32 mole) dissolved in 12ml distilled water and 12g isopropanol were required to neutralize the sulfated amide to pH 9-9.5. Yield: 135.2g of a solution containing 53% active ingredient which corresponds to 102.7% sulfation.

Example 9

Tallow isopropanolamide, 50.7g (0.154 mole) was melted and 1,1,1-trichloroethane, 5g, and isopropanol, 5.1g (0.085 mole) added with rapid agitation. Chlorosulfonic acid, 38.3g (0.32 mole) was added as described in Example 4. Sodium hydroxide, 16g in 15ml distilled water was placed in a separate vessel for neutralization of the sulfated amide. 20g isopropanol was added to reduce viscosity and facilitate neutralization. Note: The addition of alcohol to the acid sulfated alkanolamide will cause hydrolysis of sulfuric acid ester in a short period of time. Addition of alcohol to a solution of sodium hydroxide causes precipitation. This does not occur with potassium hydroxide. Yield: 142.1g of a solution containing 46.8% active ingredient which corresponds to 98.5% sulfation.

Example 10

A eutectic mixture of equal weights of tallow isopropanolamide and tallow diglycolamide has a titer of 46° C., compared to 54.5° and 58.0° C. respectively for individual amides. The use of this eutectic mixture of unhydrogenated tallow alkanolamides should facilitate sulfation on an industrial scale. This mixture is referred to as the mixed tallow alkanolamide.

Mixed tallow alkanolamide 101.7g (0.31 mole) was melted and 1,1,1-trichloroethane, 40g, was added followed by isopropanol 10g (0.17 mole). Sulfation with chlorosulfonic acid, 72.5g (0.62 mole) was carried out as described in Example 4. Potassium hydroxide, 48g (0.86 mole) dissolved in 40ml distilled water and 25g isopropanol neutralized the sulfated amide to pH 9–9.5. Yield: 247g of a solution containing 49.5% active ingredient which corresponds to a 90% yield of sulfation.

SULFATION IN THE ABSENCE OF ALCOHOL AND SOLVENT

Example 11

Tallow isopropanolamide, 100.2g (0.305 mole) was sulfated with chlorosulfonic acid, 42.7g (0.37 mole) at 55–60° C. over a period of one hour and twenty minutes. The sulfated amide was quite viscous and was heated to 60° C. so that it could be removed from the reaction flask. Hydrogen chloride vapors were removed by application of slight vacuum. Potassium hydroxide, 25g (0.45 mole) dissolved in 20ml distilled water and 20g isopropanol, was required for neutralization to pH 9–9.5. Hydrogen peroxide, 5g of a 30% solution was added to bleach the product. This product was much darker in color than those described in the previous examples. Yield: 203.1g of a solution containing 36.2% active ingredient which corresponds to 53.2% sulfation.

We claim:

1. In a process for preparing sulfated fatty alkanolamides wherein fatty acids and fatty acid esters are reacted with low molecular weight alkanolamines and the resultant fatty alkanolamide sulfated, the improvement which comprises adding from about 5 to about 15% by weight of a low molecular weight alcohol to the fatty alkanolamide and co-sulfating the alcohol and the alkanolamide with a sulfating agent, said alcohol having from 1 to 8 carbon atoms.

2. The improvement of claim 1 wherein the fatty alkanolamide is a tallow alkanolamide.

3. The improvement of claim 2 wherein the tallow alkanolamide is selected from the group consisting of tallow isopropanolamide and a mixed tallow alkanolamide, said mixed tallow alkanolamide being a mixture of equal weights of tallow isopropanolamide and tallow diglycolamide.

4. The improvement of claim 3 wherein the tallow alkanolamide is tallow isopropanolamide and the alcohol is selected from the group consisting of methanol and isopropanol.

5. The improvement of claim 4 wherein the low molecular weight alcohol is methanol.

6. The improvment of claim 4 wherein the low molecular weight alcohol is isopropanol.

7. The improvement of claim 3 wherein the tallow alkanolamide is a mixed tallow alkanolamide.

8. The improvement of claim 7 wherein the low molecular weight alcohol is isopropanol.

* * * * *